(12) United States Patent
Cheng

(10) Patent No.: US 10,004,781 B2
(45) Date of Patent: Jun. 26, 2018

(54) PRESCRIPTION OF INTRAVENOUS MEDICATION FOR BLOCKING HEROIN OR MORPHINE INTOXICATION PATH AND USING THEREOF

(71) Applicant: En-Che Cheng, Kaohsiung (TW)

(72) Inventor: En-Che Cheng, Kaohsiung (TW)

( * ) Notice: Subject to any disclaimer, the term of this patent is extended or adjusted under 35 U.S.C. 154(b) by 144 days.

(21) Appl. No.: 15/000,093

(22) Filed: Jan. 19, 2016

(65) Prior Publication Data

US 2017/0157209 A1    Jun. 8, 2017

(30) Foreign Application Priority Data

Dec. 4, 2015    (TW) .............................. 104140659 A

(51) Int. Cl.

| | |
|---|---|
| A61K 31/70 | (2006.01) |
| A61K 31/553 | (2006.01) |
| A61K 31/51 | (2006.01) |
| A61K 31/44 | (2006.01) |
| A61K 31/34 | (2006.01) |
| A61K 31/035 | (2006.01) |
| A61K 38/17 | (2006.01) |
| A61K 35/30 | (2015.01) |
| A61K 31/4015 | (2006.01) |
| A61K 31/4164 | (2006.01) |
| A61K 31/439 | (2006.01) |
| A61K 31/375 | (2006.01) |
| A61K 31/407 | (2006.01) |
| A61K 45/06 | (2006.01) |
| A61K 9/00 | (2006.01) |
| A61K 31/4515 | (2006.01) |
| A61K 31/5513 | (2006.01) |
| A61K 31/714 | (2006.01) |

(52) U.S. Cl.
CPC ........ *A61K 38/1709* (2013.01); *A61K 9/0019* (2013.01); *A61K 31/375* (2013.01); *A61K 31/407* (2013.01); *A61K 31/4015* (2013.01); *A61K 31/4164* (2013.01); *A61K 31/439* (2013.01); *A61K 31/4515* (2013.01); *A61K 31/51* (2013.01); *A61K 31/553* (2013.01); *A61K 31/5513* (2013.01); *A61K 31/714* (2013.01); *A61K 35/30* (2013.01); *A61K 45/06* (2013.01)

(58) Field of Classification Search
CPC ...... A61K 31/714; A61K 31/51; A61K 31/46; A61K 31/415; A61K 31/31; A61K 31/40; A61K 31/375; A61K 31/02; C07D 281/10
USPC .... 514/52, 211.09, 276, 304, 396, 413, 474, 514/744
See application file for complete search history.

(56) References Cited

U.S. PATENT DOCUMENTS

| | | | | |
|---|---|---|---|---|
| 4,647,460 | A * | 3/1987 | Lee ..................... | A61K 36/23 424/728 |
| 5,413,993 | A * | 5/1995 | Soma .................. | A61K 31/715 424/93.4 |
| 6,121,291 | A * | 9/2000 | Gleason ............. | A61K 31/4525 514/321 |
| 6,759,399 | B1 * | 7/2004 | Petit ..................... | A61K 31/58 514/169 |
| 2009/0221490 | A1 * | 9/2009 | Gulati ................ | G01N 33/9486 514/17.5 |
| 2010/0144754 | A1 * | 6/2010 | Peltz .................. | A61K 31/4178 514/255.04 |

* cited by examiner

*Primary Examiner* — Raymond J Henley, III
(74) *Attorney, Agent, or Firm* — Alan D. Kamrath; Kamrath IP Lawfirm, P.A.

(57) ABSTRACT

A prescription of intravenous medication and its treatment method block heroin or morphine intoxication. The prescription of intravenous infusion includes Cerebrolysin, Piracetam, Cimetidine, Scopolamine Butylbromide, Nefopam, B.C Complex, Vitamin B1, Ascorbic Acid, Ketorolac, Guronsan, Hyoscine Butylbromide and Sukerin. The prescription activates a patient's liver and circulatory system to block drug intoxication. The treatment method for blocking drugs includes an acute withdrawal part, with the prescription of intravenous infusion injected and with the timing of drug administration and the safe dosage controlled according to clinical symptoms. An appropriate amount of a supplementary medicine such as Haloperidol is added, and the processes of detoxication, relieving symptoms, suppressing restlessness, and sobering are conducted to block acute withdrawal symptoms of an acute withdrawal addict quickly and successfully.

18 Claims, 2 Drawing Sheets

| Prescription of Intravenous Infusion ||
|---|---|
| Ingredient | % of Dosage |
| Cerebrolysin | 3~13% |
| Piracetam | 3~13% |
| Cimetidine | 3~13% |
| Scopolamine Butylbromide | 3~13% |
| Nefopam | 3~13% |
| B.C Complex | 3~13% |
| Vitamin B1 | 3~13% |
| Ascorbic Acid | 3~13% |
| Ketorolac | 3~13% |
| Guronsan | 3~13% |
| Hyoscine Butylbromide | 3~13% |
| Sukerin | 3~13% |

*FIG. 1*

PRESCRIPTION OF INTRAVENOUS MEDICATION FOR BLOCKING HEROIN OR MORPHINE INTOXICATION PATH AND USING THEREOF

BACKGROUND OF THE INVENTION

Field of the Invention

The present invention relates to a prescription of intravenous medication for blocking a heroin or morphine intoxication path and its using and, more particularly, to the prescription of intravenous infusion and its using. The intravenous medication is injected to a patient to activate the patient's liver and circulatory system, while a doctor and/or a nurse controls the timing of drug administration and the safe dosage to block acute withdrawal symptoms of an acute withdrawal addict quickly and successfully by the processes of detoxication, relieving symptoms, suppressing restlessness, and sobering.

Description of the Related Art

In medicine, heroin and morphine may be used as potent analgesic drugs for alleviating pains caused by heart disease, trauma, surgery, etc. Since heroin and morphine have a strong addictive property, they are also used as potent drugs. When use at an early time, a user feels happy, peaceful and high, but fails to concentrate. The user's body cannot function normally twelve hours after taking the drugs, and withdrawal symptoms, including being tense, being unable to sleep, sweating, having upset stomach, having pains in limbs, cramps, etc., show up. These withdrawal symptoms continue for three to five days. The longer the user takes heroin/morphine, the longer the withdrawal symptoms last. An overdose of heroin/morphine may cause acute poisoning with symptoms including drowsiness, respiratory depression, hypotension, and the pupils becoming smaller. With repeated use of heroin/morphine, high psychological and physiological dependences occur, and the heroin/morphine addict's body adapts to the presence of the drugs and must continue to increase the amount of dose in order to obtain the same effect. After taking the drugs for a long term, an addict stopping taking the drugs will have withdrawal symptoms such as drug craving, anxiety, crying, sweating, runny nose, irritability, shivering, chill, loss of appetite, diarrhea, body curl, cramp, etc. Thus, it is very difficult for addicts to withdraw. It is very difficult to block the use of drugs by traditional rehabilitation methods that adopt tranquilizers and antidepressants.

In view of the aforementioned problem that it is difficult for heroin or morphine addicts to block the drugs, the present invention provides a feasible solution to help the addicts or patients to block heroin or morphine successfully.

SUMMARY OF THE INVENTION

Therefore, it is a primary objective of the present invention to provide a prescription of intravenous infusion for blocking heroin or morphine addiction.

To achieve the aforementioned objective, the present invention provides a prescription of intravenous infusion for blocking heroin or morphine addiction, and the prescription comprises the following ingredients: Cerebrolysin, Piracetam, Cimetidine, Scopamine Butylbromide, Nefopam, B.C Complex, Vitamin B1, Ascorbic Acid, Ketorolac, Guronsan, Hyoscine Butylbromide and Sukerin. The Cerebrolysin occupies 3~13% of the dosage; the Piracetam occupies 3~13% of the dosage; the Cimetidine occupies 3~13% of the dosage; the Scopolamine Butylbromide occupies 3~13% of the dosage; the Nefopam occupies 3~13% of the dosage; the B.C Complex occupies 3~13% of the dosage; the Vitamin B1 occupies 3~13% of the dosage; the Ascorbic Acid occupies 3~13% of the dosage; the Ketorolac occupies 3~13% of the dosage; the Guronsan occupies 3~13% of the dosage; the Hyoscine Butylbromide occupies 3~13% of the dosage; and the Sukerin occupies 3~13% of the dosage. The prescription of intravenous infusion can activate a patient's liver and circulatory system, to eliminate the ingredients of heroin/morphine in the patient's body, and to block the drugs.

Another objective of the present invention is to provide a treatment method for blocking heroin or morphine addiction, and the treatment method includes an actual withdrawal part and an outpatient part. The acute withdrawal part includes the following three stages:

The first stage is an acute withdrawal stage and is further divided into three phases of treatment. The first phase treatment applies 6 bottles of the aforementioned prescription of intravenous infusion daily according to a standard treatment record sheet, and clinical doctors add other corresponsive prescriptions of injection to each bottle of the prescription of intravenous infusion according to the level of a patient's clinical symptoms to primarily activate physiological withdrawal. The second phase applies 6~9 bottles of the prescription of intravenous infusion, since the patient's drug has been eliminated quickly, the drug has dependence, the patient's physiological and neurotransmitter system is still not recovered, and the clinical treatment may cause restlessness and instability, so that a prescription of Haloperidol and Diazepam is applied according to the level of the patient's restlessness. The third phase treatment applies 9~18 bottles of the prescription of intravenous infusion and continues applying the prescription according to a standard course to complete blocking the drugs.

The second stage is a consciousness recovery stage, with 2 Amp of Akineton added slowly into the prescription of intravenous infusion to help the patient to recover consciousness.

The third stage is a body recovery stage which completes the treatment for acute withdrawal of heroin damage.

In an outpatient part, the prescription of intravenous infusion, Nefopam, Sukerin, Vitamin B12, Cerebrolysin and Guronsan are applied to the patient to achieve the effects of relieving withdrawal symptoms, assisting circulation and metabolism, and enhancing the withdrawal, to block the addiction successfully. The patient's drug response condition can be detected by a blood test to block the use of drugs successfully.

BRIEF DESCRIPTION OF THE DRAWINGS

FIG. 1 is a table listing the composition and dosage of a prescription of intravenous infusion in accordance with a preferred embodiment of the present invention.

DETAILED DESCRIPTION OF THE PREFERRED EMBODIMENTS

Figure 2:
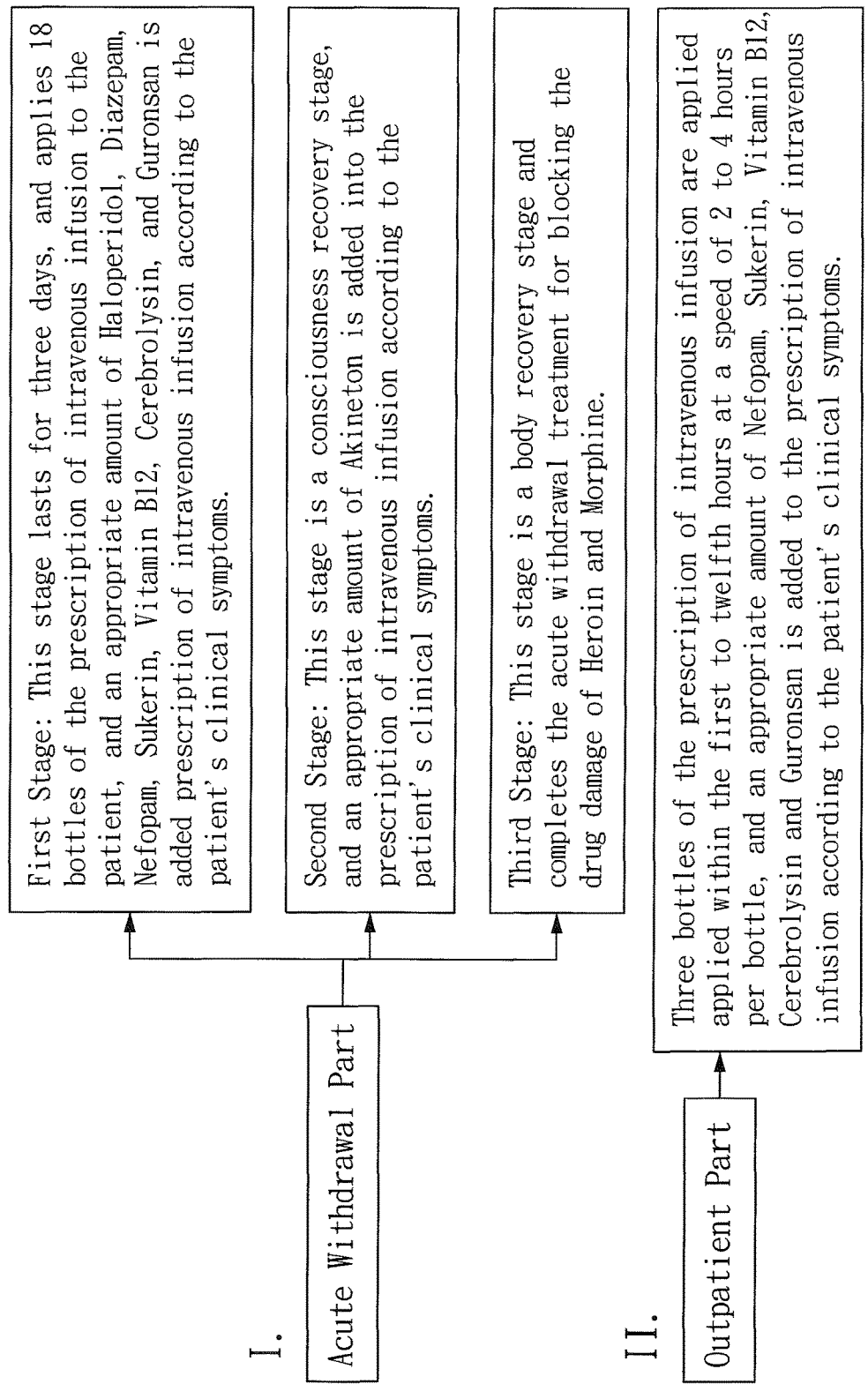
FIG. 2 is a flow chart of a treatment method in accordance with a preferred embodiment of the present invention.

The technical characteristics, contents, advantages and effects of the present invention will be apparent with the detailed description of preferred embodiments accompanied with related drawings as follows.

With reference to FIG. 1 for a prescription of intravenous infusion of the present invention for blocking heroin or morphine addiction, the invention focuses on the activation of a patient's liver and circulatory system to block the heroin or morphine addiction. The prescription of intravenous infusion comprises the following drugs with their names and dosages:

Cerebrolysin (drug name and generic name) occupies 3~13% of the dosage, and it is a medicine for curing a patient's nervous system.

Piracetam (drug name and generic name) occupies 3~13% of the dosage, and it is a medicine for curing a patient's blood system.

Cimetidine (drug name and generic name) occupies 3~13% of the dosage, and it is a medicine for curing a patient's digestive system.

Scopolamine Butylbromide (drug name and generic name) occupies 3~13% of the dosage, and it is a medicine for curing a patient's peripheral nervous system as well as is a parasympathetic inhibitor.

Nefopam (having a drug name "Nefopam HCL" and a generic name "Nefopam") occupies 3~13% of the dosage, and it is a medicine for curing a patient's central nervous system.

B.C Complex (drug name and generic name) occupies 3~13% of the dosage, and it is a vitamin/fat-soluble vitamin complex.

Vitamin B1 (drug name and generic name) occupies 3~13% of the dosage.

Ascorbic Acid (drug name and generic name) occupies 3~13% of the dosage.

Ketorolac (drug name and generic name) occupies 3~13% of the dosage, and it is a non-steroidal anti-inflammatory analgesic agent for curing a patient's body pains.

Guronsan occupies 3~13% of the dosage, and it is a hepatotropic agent for curing a patient's drug intoxication.

Hyoscine Butylbromide (drug name and generic name) occupies 3~13% of the dosage, and it is a digestive system drug/anticonvulsant for relieving a patient's digestive track spasm.

Sukerin occupies 3~13% of the dosage, and it is used for relieving a patient's peripheral pains.

The prescription of intravenous infusion focuses on the activation of a patient's liver and circulatory system, and the prescription of intravenous infusion is applied and injected to the patient, so that the heroin/morphine drugs in the patient's body is eliminated quickly to block addition. Different dosages may be applied according to the patient's different symptoms, and doctors and nurses control the timing of drug administration and the safe dosage to achieve blocking addiction.

With reference to FIG. 2 for a treatment method of heroin or morphine addiction by using the prescription of intravenous infusion of the present invention, the treatment method comprises an acute withdrawal part and an outpatient part.

I. The Acute Withdrawal Part Includes the Following Stages Carried Out Sequentially:

1. The first stage is an acute withdrawal stage lasting for three days. 6 bottles of the prescription of intravenous infusion are applied daily according to a standard treatment record sheet, and the prescription of intravenous infusion is applied at a speed of 4 hours per bottle. The first stage includes the following three using treatment phases:

(1) The first phase treatment (from the $4^{th}$ hour to the $18^{th}$ hour) primarily eliminates heroin/morphine in the patient's body quickly. The $1^{st}$ to $5^{th}$ bottles of the prescription of intravenous infusion are applied to the patient, and a clinical doctor adds another supplementary prescription to the prescription of intravenous infusion according to the level of the patient's clinical symptoms. For example, if the level of the patient's clinical symptoms is ordinary, then 2 Amp of Haloperidol and 1 Amp of Diazepam will be added to the prescription of intravenous infusion; if the level of the patient's clinical symptoms is mild, then 2 Amp of Haloperidol will be added to the prescription of intravenous infusion the prescription of intravenous infusion; if the level of the patient's clinical symptoms includes severe pains all over the body, then 2 Amp of Nefopam will be slowly added to the prescription of intravenous infusion; if the level of the patient's clinical symptoms includes moderate pains all over the body, then 1 Amp of Nefopam will be slowly added in the prescription of intravenous infusion; and if the level of the patient's clinical symptoms includes serious yawn, tears, and relief of withdrawal symptoms, then 1~2 Amp of Sukerin will be added to the prescription of intravenous infusion, or Vitamin B12 is applied to achieve the effects of improving the detoxication, blocking the damage path of heroin/morphine, and activating the patient's liver and relieving neuropathic pains. Cerebrolysin and Guronsan may also be supplemented to assist circulation and metabolism and enhance the physiological detoxication function.

(2) The second phase treatment (from the $18^{th}$ hour to the $36^{th}$ hour) applies the $6^{th}$ to $9^{th}$ bottles of the prescription of intravenous infusion. After the first phase treatment, the heroin/morphine in the patient's body has been eliminated quickly, and the patient's drug dependence is relieved quickly. However, the patient's neurotransmitter system is still not recovered physiologically and cannot function normally. Since the patient is physically, mentally, and subconsciously under stress for a long time, the patient becomes restless and unstable and has encounters disordered sleep. The repeated unconscious restless movement will continue for 18 hours. Now, the following supplementary medicine other than the prescription of intravenous infusion may be applied to the patient according to the level of the patient's restlessness. If the patient is in serious restlessness, then 3 Amp of Haloperidol and 2 Amp of Diazepam will be added to the prescription of intravenous infusion; and if the patient is in moderate restlessness, then 2 Amp of Haloperidol and 2 Amp of Diazepam will be added to the prescription of intravenous infusion.

(3) The third phase treatment (from the 36th hour to the 72nd hour) applies the 9th to 18th bottles of the prescription of intravenous infusion to the patient to continue completing the acute withdrawal of heroin and morphine up to 70% to 95% and to block the drug damage of heroin and morphine.

2. The second stage is a one-day consciousness recovery period (from the $72^{nd}$ hour to the $96^{th}$ hour) and adds 2 Amp of Akineton (Drug Name: Akineton, and Generic Name: BIPERIDEN HCL) to the prescription of intravenous infusion, so that the patient recovers the consciousness normally and quickly within 24 hours.

3. The third stage (from the $96^{th}$ hour to the $120^{th}$ hour) is a body recovery stage, and the basic functions of the patient's body enter into the subsequent life rebuilding stage.

The present invention uses 5 days as a course to complete the acute withdrawal treatment of blocking the drug damage of heroin.

II. Outpatient Part:

The standard period of the outpatient part is 6~12 hours, and 3 bottles of the prescription of intravenous infusion are used for one course. The prescription of intravenous infusion is injected at a speed of 2 to 4 hours per bottle according to the standard treatment record sheet, and the following prescription is applied slowly according to the patient's symptoms. For example, if the patient has a pain symptom, then 1~2 Amp of Nefopam will be slowly added to the prescription of intravenous infusion; if the patient has yawn and tears symptoms, then 1~2 Amp of Sukerin will be slowly added to the prescription of intravenous infusion. In addition, Vitamin B12 may be applied to the patient at an appropriate time to achieve the effects of improving the detoxication, blocking the drug damage path of heroin or morphine drug damage, and activating the patient's liver and relieve neuropathic pains. Cerebrolysin and Guronsan may also be supplemented at an appropriate time to assist the patient's circulation and metabolism and enhance the physiological detoxication function.

The prescription of intravenous infusion and the treatment method applying the prescription of intravenous infusion in accordance with of the present invention activate the patient's liver and circulatory system, and doctors and nurses control the timing of drug administration and the safe dosage to block the patient's addiction successfully. A blood test is provided for showing the patient's drug response condition, to block the addiction successfully.

While the invention has been described by means of specific embodiments, numerous modifications and variations could be made thereto by those skilled in the art without departing from the scope and spirit of the invention set forth in the claims.

What is claimed is:

1. An intravenous infusion composition for blocking heroin or morphine intoxication, comprising a plurality of ingredients consisting of Cerebrolysin, Piracetam, Cimetidine, Scopolamine Butylbromide, Nefopam, B.C Complex, Vitamin B1, Ascorbic Acid, Ketorolac, Guronsan, Hyoscine Butylbromide, and Sukerin.

2. The intravenous infusion composition according to claim 1, wherein each ingredient occupies 3~13% of a dosage.

3. A method for blocking heroin or morphine intoxication comprising administering the intravenous infusion composition according to claim 2, further including the administration of an an acute withdrawal part wherein said part is administered during a patient's acute withdrawal period, with the acute withdrawal part comprising the following treatment stages:

a first phase treatment of a first stage which comprises the administration of the intravenous infusion composition to the patient to eliminate heroin/morphine from the patient's body, and administering a first supplementary composition for improving detoxification, blocking a damage path of the heroin or morphine intoxication, and activating the patient's liver to relieve neuropathic pains to the intravenous infusion composition;

a second phase treatment of the first stage continues in which the administration of the intravenous infusion composition is continued to be administered to the patient, and further comprising administering Haloperidol and Diazepam to the patient according to the level of the patient's restlessness;

a third phase treatment of the first stage wherein the intravenous infusion is continued to be administered so as to complete an acute withdrawal of heroin and morphine at percentages of up to 70% to 95%, wherein damage to the brain caused by heroin and morphine is blocked; and a second stage of treatment wherein the intravenous infusion is continued to be administered to the patient, further comprising administering Akineton (Biperiden HCL) in the intravenous infusion, whereby the patient's consciousness recovers to what is normal for the patient.

4. The method according to claim 3, wherein the first phase treatment of the first stage takes place within a treatment period of from the 4 hours to 18 hours and and encompasses the administration of the first dosage amount to the fifth dosage amount of the intravenous infusion composition to the patient, and with the first supplementary composition consisting of Haloperidol, Diazepam, Nefopam, and Sukerin administered into the intravenous infusion composition according to the level of patient's clinical symptoms.

5. The method according to claim 4, wherein the first phase treatment of the first stage administers the first supplementary composition consisting of Vitamin B12, and further comprising administering a second supplementary composition consisting of Cerebrolysin and Guronsan to the patient to assist circulation and metabolism, and enhance physiological detoxication function.

6. The method according to claim 4, wherein the second phase treatment of the first stage takes place within a treatment period of from 18 hours to 36 hours and applies the sixth dosage to the ninth dosage of the intravenous infusion composition to the patient.

7. The method according to claim 6, wherein the third phase treatment of the first stage takes place within a treatment period of from 36 hours to 72 hours and administers the ninth dosage to the eighteenth dosage of the intravenous infusion composition to the patient.

8. The method according to claim 7, wherein the second stage takes place within a treatment period of from the 72 hours to 96 hours.

9. The method according to claim 3, further comprising the administration of an outpatient part which is administered during the patient's acute withdrawal period and with a standard period of 6~12 hours, and three dosages of the intravenous infusion composition being used as a course, and the intravenous infusion composition being injected at a speed of 2~4 hours per dosage according to a standard treatment record sheet, and with the first supplementary composition together with the intravenous infusion composition being injected by intravenous infusion according to the patient's symptoms.

10. The method according to claim 9, wherein the outpatient part administers a second supplementary composition consisting of Nefopam and Sukerin into the intravenous infusion composition according to the patient's symptoms, and supplies Vitamin B12, Cerebrolysin and Guronsan to the patient.

11. A method for blocking heroin or morphine intoxication comprising administering the intravenous infusion composition according to claim 1, further including the administration of an acute withdrawal part wherein said part is administered during a patient's acute withdrawal period, with the acute withdrawal part comprising the following treatment stages:

a first phase treatment of a first stage which comprises the administration of the intravenous infusion composition to the patient to eliminate heroin/morphine from the patient's body, and administering a first supplementary composition for improving detoxification, blocking a damage path of the heroin or morphine intoxication, and activating the patient's liver to relieve neuropathic pains to the intravenous infusion composition;

a second phase treatment of the first stage continues in which the administration of the intravenous infusion composition is continued to be administered to the patient, and further comprising administering Haloperidol and Diazepam to the patient according to the level of the patient's restlessness;

a third phase treatment of the first stage wherein the intravenous infusion is continued to be administered so as to complete an acute withdrawal of heroin and morphine at percentages of up to 70% to 95%, wherein damage to the brain caused by heroin and morphine is blocked; and a second stage of treatment wherein the intravenous infusion is continued to be administered to the patient, further comprising administering Akineton (Biperiden HCL) in the intravenous infusion, whereby the patient's consciousness recovers to what is normal for the patient.

12. The method according to claim 11, wherein the first phase treatment of the first stage takes place within a treatment period of from 4 hours to 18 hours and and encompasses the administration of the first dosage amount to the fifth dosage amount of the intravenous infusion composition to the patient, and with the first supplementary composition consisting of Haloperidol, Diazepam, Nefopam, and Sukerin administered into the intravenous infusion composition according to the level of patient's clinical symptoms.

13. The method according to claim 12, wherein the first phase treatment of the first stage administers the first supplementary composition consisting of Vitamin B12, and further comprising administering a second supplementary composition consisting of Cerebrolysin and Guronsan to the patient to assist circulation and metabolism, and enhance physiological detoxication function.

14. The method according to claim 12, wherein the second phase treatment of the first stage takes place within a treatment period of from 18 hours to 36 hours and applies the sixth dosage to the ninth dosage of the intravenous infusion composition to the patient.

15. The method according to claim 14, wherein the third phase treatment of the first stage takes place within a treatment period of from 36 hours to 72 hours and administers the ninth dosage to the eighteenth dosage of the intravenous infusion composition to the patient.

16. The method according to claim 15, wherein the second stage takes place within a treatment period of from 72 hours to 96 hours.

17. The method according to claim 11, further comprising the administration of an outpatient part which is administered during the patient's acute withdrawal period and with a standard period of 6~12 hours, and three dosages of the intravenous infusion composition being used as a course, and the intravenous infusion composition being injected at a speed of 2~4 hours per dosage according to a standard treatment record sheet, and with the first supplementary composition together with the intravenous infusion composition being injected by intravenous infusion according to the patient's symptoms.

18. The method according to claim 17, wherein the outpatient part administers a second supplementary composition consisting of Nefopam and Sukerin into the intravenous infusion composition according to the patient's symptoms, and supplies Vitamin B12, Cerebrolysin and Guronsan to the patient.

* * * * *